United States Patent
Holt

(10) Patent No.: US 9,970,890 B2
(45) Date of Patent: May 15, 2018

(54) METHOD AND APPARATUS PERTAINING TO NON-INVASIVE IDENTIFICATION OF MATERIALS

(75) Inventor: Kevin M. Holt, Chicago, IL (US)

(73) Assignee: Varex Imaging Corporation, Salt Lake City, UT (US)

(*) Notice: Subject to any disclaimer, the term of this patent is extended or adjusted under 35 U.S.C. 154(b) by 51 days.

(21) Appl. No.: 13/277,833

(22) Filed: Oct. 20, 2011

(65) Prior Publication Data

US 2013/0101156 A1    Apr. 25, 2013

(51) Int. Cl.
*G06K 9/00* (2006.01)
*G01N 23/06* (2018.01)

(52) U.S. Cl.
CPC ....... *G01N 23/06* (2013.01); *G01N 2223/405* (2013.01); *G01N 2223/423* (2013.01)

(58) Field of Classification Search
USPC ............ 382/100, 103, 108, 109, 131, 132; 378/45, 53, 57, 83, 88
See application file for complete search history.

(56) References Cited

U.S. PATENT DOCUMENTS

| | | | | |
|---|---|---|---|---|
| 5,841,046 A * | 11/1998 | Rhodes | ........ | B22F 9/082 75/243 |
| 8,184,769 B2 * | 5/2012 | Fox et al. | ........ | 378/53 |
| 8,422,826 B2 * | 4/2013 | Holt | ........ | 382/294 |
| 8,508,545 B2 * | 8/2013 | Holt | ........ | 345/589 |
| 2003/0194053 A1 * | 10/2003 | Schramm et al. | ........ | 378/45 |
| 2007/0183568 A1 * | 8/2007 | Kang et al. | ........ | 378/57 |
| 2009/0041185 A1 * | 2/2009 | Might et al. | ........ | 378/57 |
| 2010/0310042 A1 * | 12/2010 | Fox et al. | ........ | 378/53 |
| 2010/0310175 A1 * | 12/2010 | Holt | ........ | 382/195 |
| 2011/0096083 A1 * | 4/2011 | Schultz | ........ | 345/583 |
| 2011/0116596 A1 * | 5/2011 | Sommer et al. | ........ | 378/53 |
| 2011/0129066 A1 * | 6/2011 | Statham et al. | ........ | 378/88 |
| 2011/0280440 A1 * | 11/2011 | Holt | ........ | 382/103 |

(Continued)

FOREIGN PATENT DOCUMENTS

| | | |
|---|---|---|
| JP | 2004-174253 A | 6/2004 |
| JP | 2004-174261 A | 6/2004 |

(Continued)

OTHER PUBLICATIONS

NPL Website, Published Aug. 31, 2007: http://www.classzone.com/books/earth_science/terc/content/investigations/esu101/esu101page05.cfm?chapter_no=investigation.*

(Continued)

*Primary Examiner* — Vikkram Bali
(74) *Attorney, Agent, or Firm* — Fitch, Even, Tabin & Flannery LLP

(57) ABSTRACT

A control circuit having access to information regarding a plurality of models for different materials along with feasibility criteria processes imaging information for an object (as provided, for example, by a non-invasive imaging apparatus) to facilitate identifying the materials as comprise that object by using the plurality of models to identify candidate materials for portions of the imaging information and then using the feasibility criteria to reduce the candidate materials by avoiding at least one of unlikely materials and combinations of materials to thereby yield useful material-identification information.

12 Claims, 5 Drawing Sheets

(56) References Cited

U.S. PATENT DOCUMENTS

2012/0106816 A1* 5/2012 Bernard De Man
 et al. .............................. 382/131
2013/0076913 A1* 3/2013 Xu et al. ....................... 348/169

FOREIGN PATENT DOCUMENTS

JP  2009-261519 A  11/2009
WO 2008-075595 A1  6/2008

OTHER PUBLICATIONS

Alvarez, Robert E. et al., "Energy-Selective Reconstructions in X-ray Computerized Tomography," Phys. Med. Biol., vol. 21, No. 5, pp. 733-744; 1976.
Srebro, Nathan et al., "Weighted Low-Rank Approximations," Proceedings of the Twentieth International Conference on Machine Learning (ICML-2003), Washington DC; 8 pages; 2003.
Holt, Kevin M., "Angular Regularization of Vector-Valued Signals," 2011 IEEE International Conference on Acoustics, Speech and Signal Processing (ICASSP); May 2011, Prague, Czech Republic; 4 pages.
Na, Sun Hee; Authorized officer; PCT Search Report and Written Opinion from related application No. PCT/US2012/061334 dated Mar. 4, 2013; 8 pages.

* cited by examiner

METHOD AND APPARATUS PERTAINING TO NON-INVASIVE IDENTIFICATION OF MATERIALS

TECHNICAL FIELD

This invention relates generally to the identification of materials and more particularly to the identification of materials by use of non-invasive imaging methodologies.

BACKGROUND

The capture of radiation-detection views of a given object using penetrating energy (such as X-rays or the like) is well known in the art. Such radiation-detection views often comprise images having areas that are relatively darker or lighter (or which otherwise contrast with respect to one another) as a function of the density, path length, and/or composition of the constituent materials that comprise the object being imaged. This, in turn, can serve to provide views of objects that are otherwise occluded from visual inspection.

The use of radiation-detection views finds myriad applications. In at least some application settings, however, merely ascertaining the presence or shape of an occluded object may be insufficient to address all attendant needs. In a security application setting, for example, objects that pose a serious security concern may share a same shape with other completely innocuous objects. In cases where the densities of such objects are similar, it can become impossible to discern from such data which constitutes a threat and which does not. A similar problem can occur for some modalities when the density and path length product for two objects is substantially the same notwithstanding that they are formed of different materials. As a simple illustration in this regard, a three inch thick piece of steel may look substantially the same using radiography as a 1.75 inch thick piece of lead notwithstanding that these two materials have considerably different densities.

There are prior art suggestions that different materials can be discriminated from one another by using two different basis functions (i.e., functions that serve to represent (exactly or approximately) given members of a class as a weighted sum thereof). A specific example in those regards suggests using information regarding soft-tissue and bone space as a two-dimensional approach to represent other materials as well. While useful to help discriminate some materials as opposed to a few selective others, the scale of the problem space can overwhelm such an approach. Presuming, for example, that there are 95 (or so) elements of potential interest, one should presumably employ 95 (or so) corresponding basis functions to have a genuinely robust mechanism to unambiguously identify all 95 (or so) elements. Accommodating such a need, however, can require an undue amount of processing time and/or processing resources.

BRIEF DESCRIPTION OF THE DRAWINGS

The above needs are at least partially met through provision of the method and apparatus pertaining to non-invasive identification of materials described in the following detailed description, particularly when studied in conjunction with the drawings, wherein.

Figure 1:
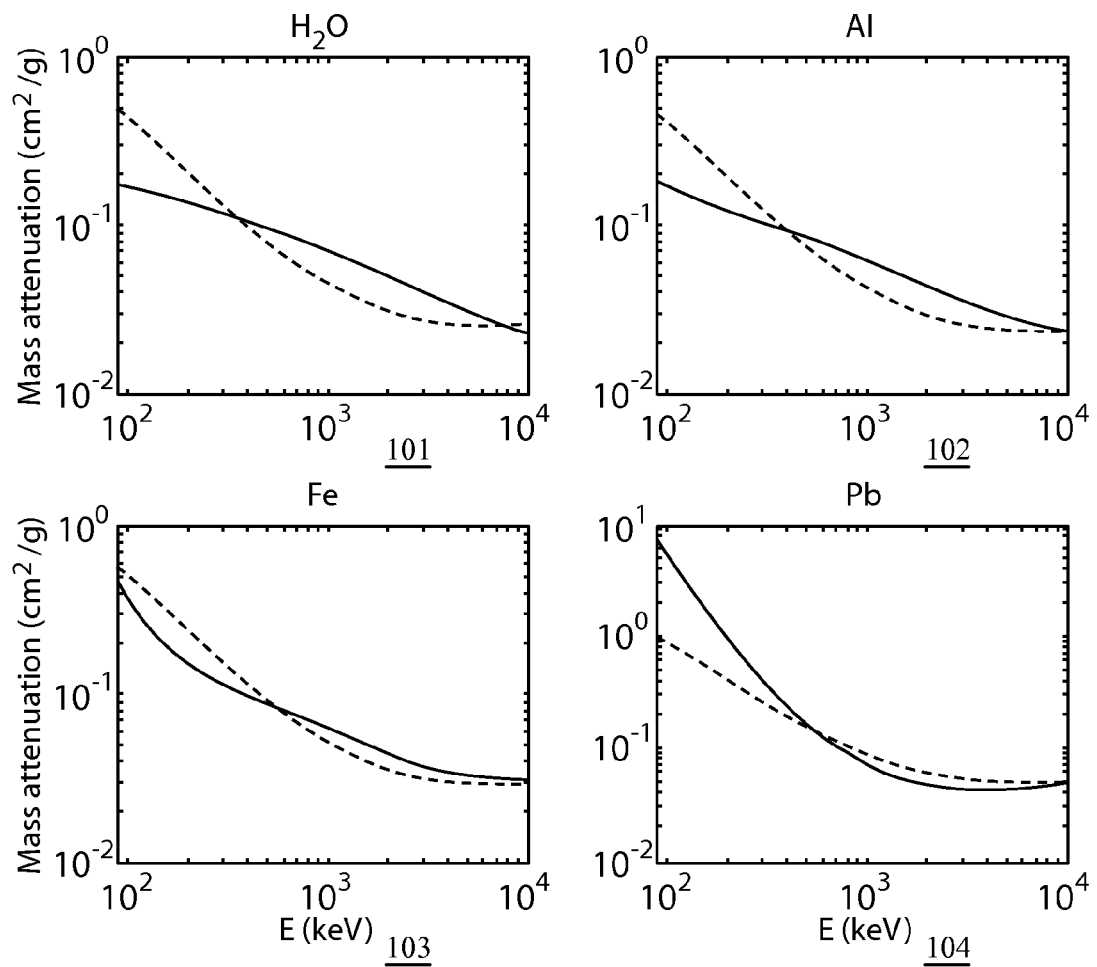
FIG. 1 comprises a series of graphs.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a control circuit having access to information regarding a plurality of models for different materials along with feasibility criteria processes imaging information for an object (as provided, for example, by a non-invasive imaging apparatus) to facilitate identifying the materials as comprise that object by using the plurality of models to identify candidate materials for portions of the imaging information and then using the feasibility criteria to reduce the candidate materials by avoiding at least one of unlikely materials and/or combinations of materials to thereby yield useful material-identification information.

By one approach, the aforementioned non-invasive imaging apparatus comprises a multi-modality apparatus that produces multiple images of overlapping portions of the object using different imaging modalities (including, for example, both active X-ray imaging and passive radiation monitoring; or, as another example, both computed tomography and magnetic-resonance imaging). By another approach, the aforementioned non-invasive imaging apparatus comprises a single-modality apparatus that uses multiple spectral channels (including, for example, X-ray imaging with multiple energies). By yet another approach, the aforementioned non-invasive imaging apparatus comprises a multi-modality apparatus where one or more modalities uses multiple spectral channels (for example, both passive radiation monitoring and multi-energy active X-ray imaging). (As used herein, this reference to "spectral channels" will be understood to include active imaging modalities that enable any selection or combination of source spectrum, external spectrum modification (through filtering and so forth), and detector response characteristics. A spectral channel for a passive imaging modality, for example, can be a combination of external spectrum modification and detector response characteristics.)

By one approach the aforementioned plurality of models include a plurality of material-imaging models that each provide a predicted result that the imaging information should present for a plurality of differing materials for a particular modality and a particular spectral channel. By one approach these materials are described by a plurality of values that each corresponds to a different basis function.

By one approach these basis functions can comprise basis materials. Given some class of materials, for example, and some imaging task, a set of materials (real or virtual) forms a basis for that class if any material that is a member of that class of materials can be represented (either exactly or approximately) as a weighted sum of materials taken from that set. More specifically, for any material property relevant to the imaging task, that property for the material that is a member of the class of materials can be represented (either exactly or approximately) as a weighted combination (usually a sum) of that property for the materials taken from that set, where the same weights (or a function of the same weights) are used for all properties. A "property" can mean a scalar number (such as atomic weight) or a more complex function or curve (such as energy-dependent attenuation curves). By way of illustration and without intending any limitations in these regards, this can comprise using four values, one for each one of four different basis materials.

By one approach, one or more of the aforementioned basis materials corresponds to an imaginary material (i.e., a "material" that comprises a mathematical construction that does not physically exist (and likely cannot physically exist) in the real world). As one illustrative example in these regards, at least one such basis material may accommodate negative properties when real-world materials may only admit of positive properties.

The aforementioned feasibility criteria can comprise, for example and at least in part, constraints regarding materials that are not physically possible and/or materials that are unlikely to be present in an absence of at least one other particular material. By another approach, in lieu of the foregoing or in combination therewith, the feasibility criteria can comprise, at least in part, constraining multiple portions of the material-identification information (such as, for example, portions that are adjacent to each other) to be similar to each other (down to and including individual image pixels).

So configured, images provided by available non-invasive imaging equipment can be significantly leveraged to facilitate identifying any of a wide variety of materials using considerably less computational power and resources than might otherwise be expected. By one approach the use of a mere four or five basis materials permits essentially any reasonably available element to be reliably discriminated under a number of challenging application settings. (As used herein, this reference to "identifying" will be understood to include both specifically and categorically determining the precise material as well as material discrimination that only results in narrowing down the material in question to a small range of candidate materials (such as a small range of the periodic table). It is also possible that this identification does not, in fact, identify discrete candidate materials as such but rather identifies, for example, a range of material possibilities. For example, this identification might comprise concluding that 90% of the material in question comes from Z=24 (i.e., chromium) to Z=30 (i.e., zinc) without specifying the relative amounts of each or any of this range of materials.)

These and other benefits may become clearer upon making a thorough review and study of the following detailed description. An illustrative process that is compatible with many of these teachings will now be presented in greater detail. It will be understood that no particular limitations are intended in view of the specificity of the following description.

The manner by which each element interacts with X-rays can be characterized by that element's mass-attenuation curve $\mu_Z(E)$, where Z is the atomic number for the element and E is energy. These attenuation curves are well known and are published, for example, in the NIST XCOM database. The attenuation curve of a compound is very closely approximated by the weighted sum of the attenuation curve of the constituent elements. That is, water has $\mu_{H2O}(E)$ very close to proportional to (2*relative weight of H)*$\mu_H(E)$+ (relative weight of O)*$\mu_O(E)$. Mixtures of materials also tend to follow this linear-sum rule. For projection modalities (i.e., modalities that project the object along some rays, such as X-ray radiography), occluded objects also tend to follow a similar linear-sum rule. For example, in radiography, the imaging system is actually sensitive to $\rho \times t \times \mu_Z(E)$, where $\rho$ is density and t is path length. Accordingly, for example, for a body of water located behind a body of steel the detector responds to $\rho_{water} \times t_{water} \times \mu_{H2O}(E) + \rho_{steel} \times t_{steel} \times \mu_{steel}(E)$, where $\mu_{H2O}(E)$ and $\mu_{steel}(E)$, are themselves compounds that can be represented as weighted sums.

By one approach, the present teachings contemplate designing a small set of basis functions A and describing each material by a relatively low-dimensional vector c, where $$\mu(E) = \sum_{k=1}^{K} A_k(E) c_k$$

For the example where K=4, each image pixel can be described by a 4-vector, which is the set of four c values. This facilitates using off-the-shelf graphics hardware that already support 4-vector processing for color bitmaps with transparency (R,G,B,$\alpha$). Significantly, the applicant has determined that one can capture in a single four-dimensional space the response of all materials in the periodic table to a useful range of X-rays.

For any element (and thus for any material, mixture, or occlusion), there is some vector c such that the approximation, $$\mu(E) \approx \sum_k A_k(E) c_k,$$

is very accurate. To build the A bases, one can establish a number of energy bins and then build a matrix with one column for each element (say, from Z=1 to 95) and one row for each energy bin (say 100-200 bins). These teachings then provide for performing a singular value decomposition (SVD) on this matrix, finding the K largest components, finding the vectors corresponding to these components, and using these vectors as A. Note that this approach can (and typically will) produce basis functions with some negative values; such basis functions can sometimes be thought of as imaginary materials (which cannot physically exist on their own, and have negative properties that cannot be negative in nature). Variations of the SVD method can also be used, including weighted singular-value decomposition (WSVD) (as described, for example, in the paper "Weighted Low-Rank Approximations" by Srebro et al. as appears in the Proceedings of the Twentieth International Conference on Machine Learning (ICML-2003), the contents of which are hereby expressly incorporated herein by this reference), where essentially the "$\approx$" above is enforced more or less strongly for different Z and E values by finding c's and A's to minimize $$\sum_{Z,E} w(Z,E) \left( \mu_Z(E) - \sum_k c_k A_k(E) \right)^2$$

where $w(Z,E)$ is a fitting weight for material Z and energy bin E. In the context of this invention, these weights can serve several purposes. For example, one might give an energy E a low weight if it cannot be produced by the imaging system, or if the detector is not sensitive to it. Similarly, one might weight energy E by the source output for that energy, or the detector's sensitivity to that energy, or both.

Such approaches can result in basis functions that are somewhat scanner dependent. Other approaches can also be used to give bases that are less scanner dependent. For example, one might include a factor of E in the weights for systems utilizing energy-integrating detectors. As another example, one might give a material a low weight if it is not likely (or possible) to be encountered in practice, or a high weight if it is a particularly important material to the imaging task (for example, a material that is particularly crucial to identify correctly). As yet another example, one might weight each energy bin E of each material Z by an inverse function of $\mu_Z(E)$ for that material and bin; very large values of μ mean that very few photons of energy E can penetrate material Z (and thus very few such photons will ever reach the detector), so if $\mu_Z(E,Z)$ is large for some (E,Z), then in many cases, in practice that $\mu_Z(E,Z)$ need not be modeled particularly accurately. Multiple weighting techniques can also be combined. For X-ray imaging, with bins ranging from 25 keV to 10 MeV, when K is 3 the approximation is generally decent. When K≥4, however, in many cases the approximation is nearly perfect (for practical purposes).

Figure 2:
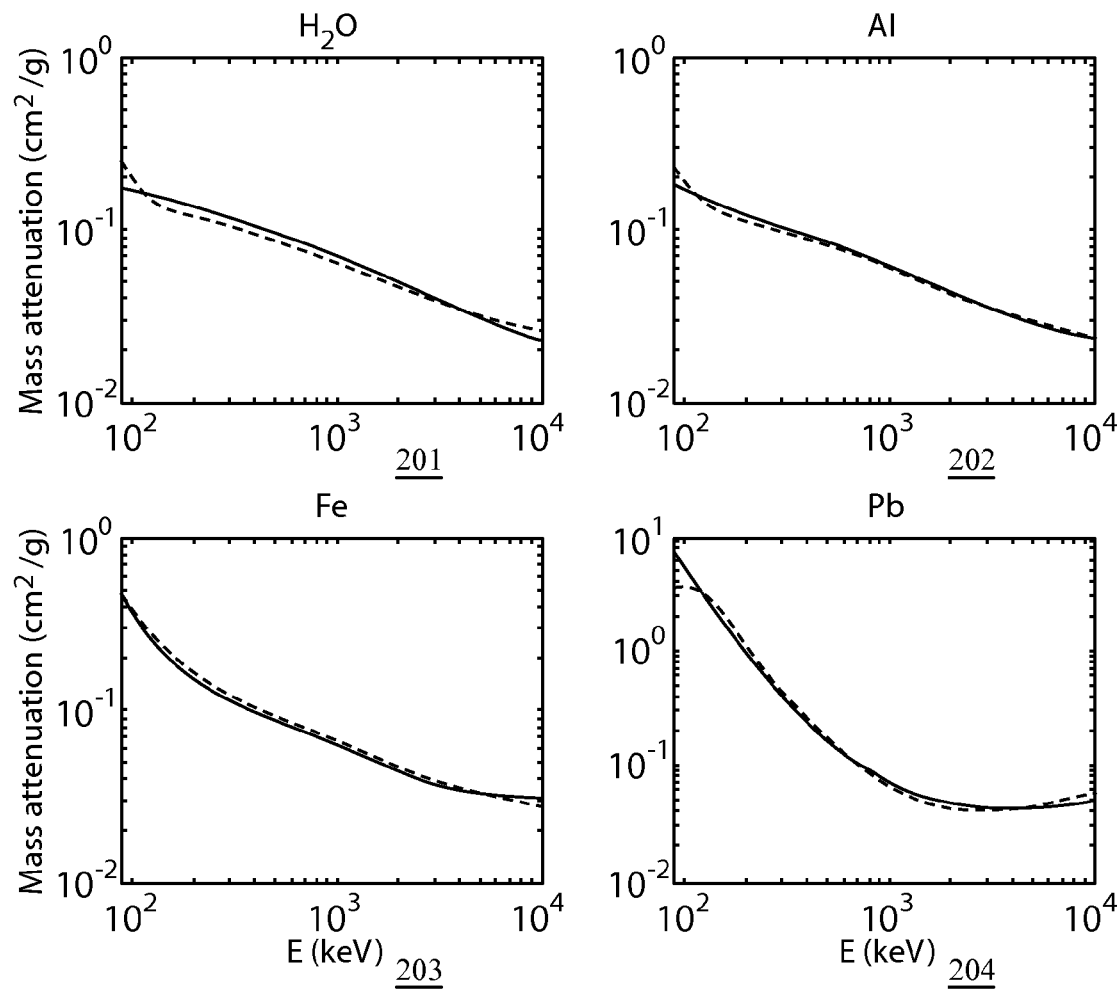
FIG. 2 comprises a series of graphs.
Figure 3:
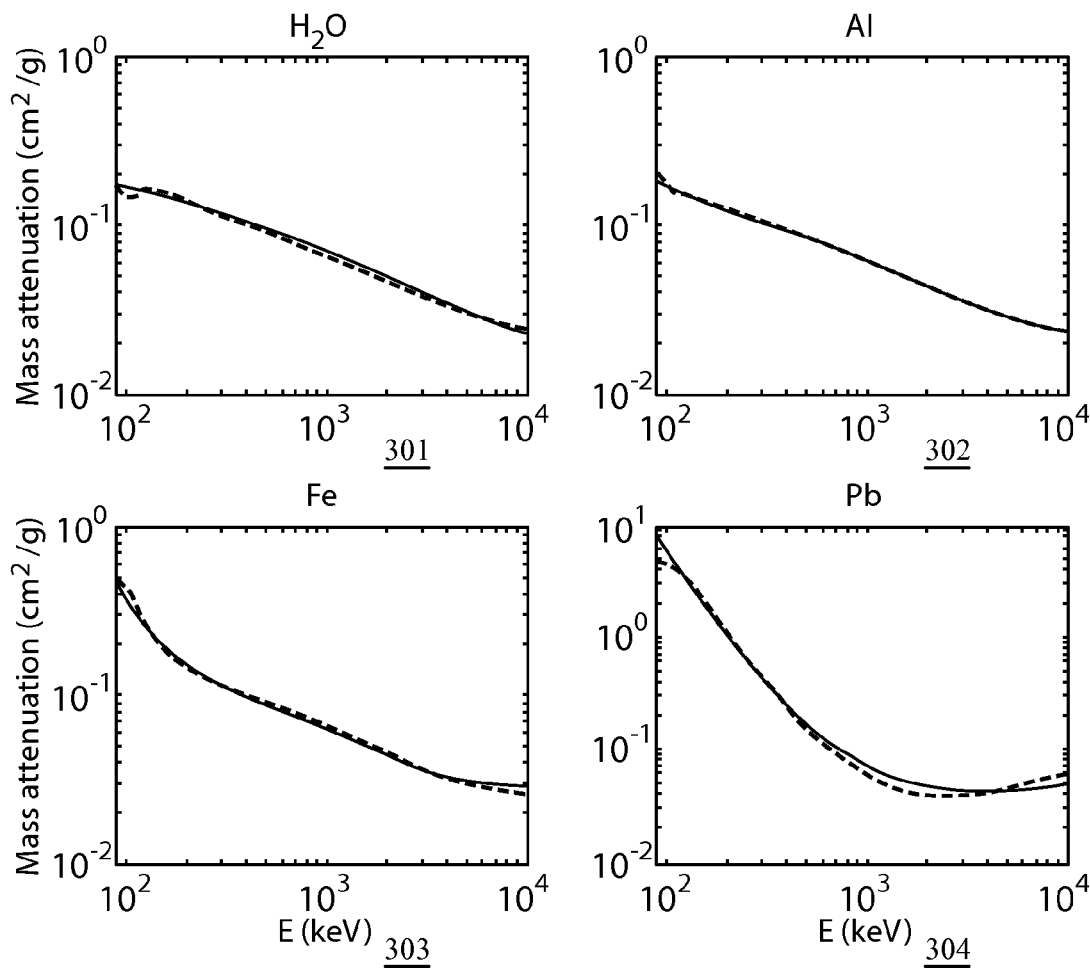
FIG. 3 comprises a series of graphs.
Figure 4:
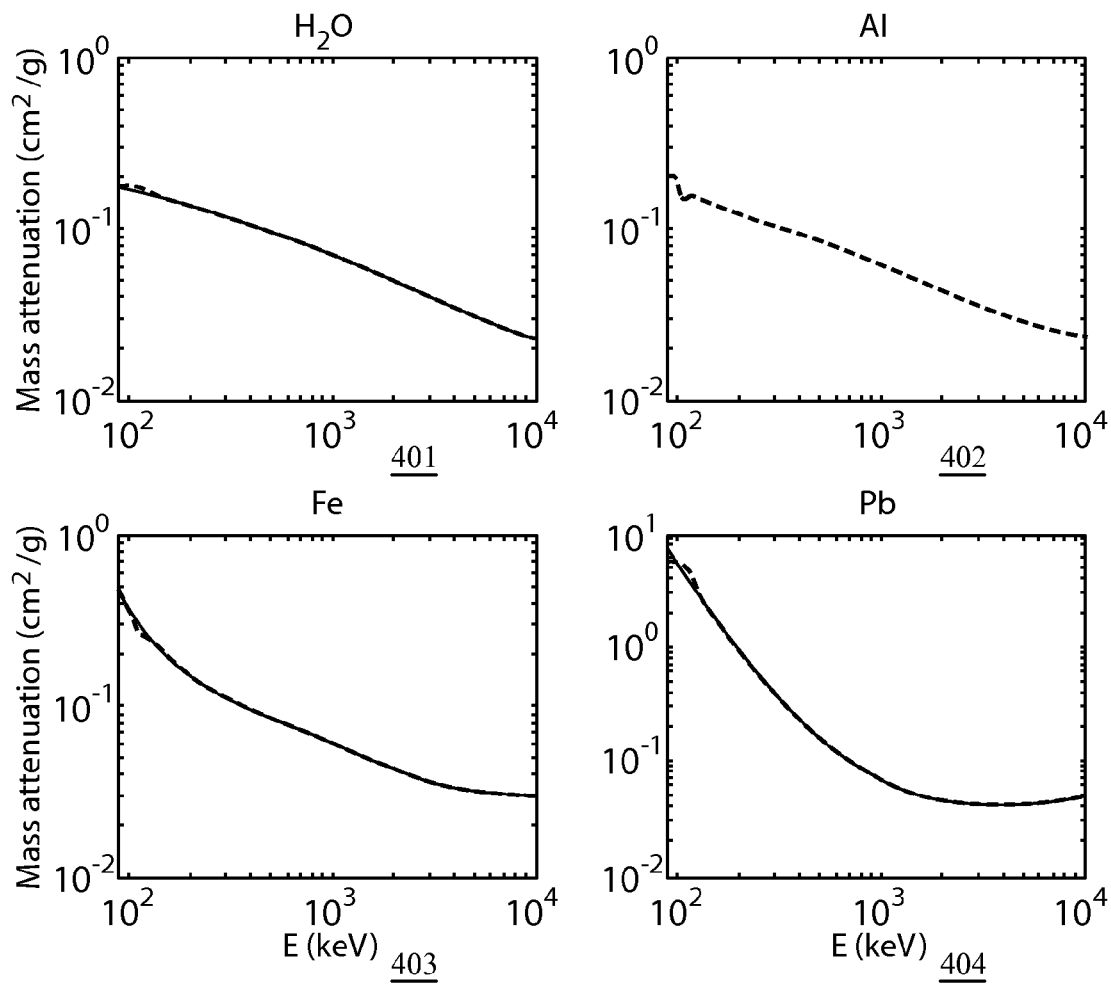
FIG. 4 comprises a series of graphs.

By way of illustration, FIG. 1 depicts characterizing curves as provided by the NIST XCOM database (as a solid line) and as represented by only a single such basis function (as a dashed line) for each of water (101), aluminum (102), iron (103), and lead (104). Since there is only a single basis function, the dashed lines all have the exact same shape (they are all scaled versions of the same single basis function), so none of them fit the solid lines particularly well. FIG. 2 presents such curves (201-204) for the same materials when using two basis functions. The quality of the matches represent an improvement over the single-basis function approach, but still does not accurately represent the attenuation curves. Further improvement is evident in FIG. 3, where the curves (301-304) for these same materials are similar in many respects when using three basis functions/vectors, but there are still several discrepancies. By the time one employs four basis functions/vectors as shown in FIG. 4 (401-404), the matches are nearly perfect. Note that the number of bases required also depends on how the bases are designed. FIGS. 1-4, for example, were made using with the WSVD approach, using weights $w(Z,E)=E/\mu_Z(E)$. Fitting with different weights, using the SVD approach, or using other bases approaches or bases sets (such as using non-imaginary or non-negative material bases) might achieve different results.

The approaches described herein employ a detailed physics model. Generally speaking, approaches described herein provide for searching for material descriptors that, when the physics model is simulated with that descriptor as the scan object, yield simulated detector responses that match the actual detector response (noting there may be more than one such solution). These teachings will accommodate a variety of approaches in these regards. By one approach, for example, the physics model can comprise an explicit physics model. By another approach the physics model can comprise an empirical-fit physics model.

With the explicit physics model approach, for each physical phenomenon that impacts the imaging process one can correlate an analytic formula for that phenomenon. These formulas are typically available in the applied physics literature. Generally speaking, these approaches make use of knowing the effective spectrum φ(E) of each spectral channel of each modality. Each effective spectrum (where "effective spectrum" characterizes the combined source and detector properties of each spectral channel) can include, for example, the source photon spectrum, source filtration, detector filtration, and detector energy-sensitivity. φ(E) can be measured through a calibration procedure, or generated through simulation (such as Monte Carlo simulation), or found through some combination of the two.

Consider the case where the material descriptors are the c vectors described earlier, and the true descriptor c for some material is known. The detector's performance can be expressed as:

$$Q = \int \varphi(E) e^{-\sum_{k=1}^{K} A_k(E) c_k} dE$$

Note that each spectral channel within each modality has its own Q function. Therefore, even when c is unknown, with several transmission measurements one can recover c exactly or nearly exactly (and thus μ(E) exactly or nearly exactly) by solving for the value of c that makes Q equal to the measured value. For example, with four spectra, there are four equations and four unknowns. Accordingly, unless some of those equations are redundant, c can be recovered exactly.

For an empirical-fit model, instead of using models known to describe physical processes, these teachings use a generic fitting function:

$$Q = f_\theta(c)$$

This function maps c (a 4-vector) to Q (usually a scalar). In general, this function has some set of parameters θ that are calibrated by performing a calibration scan of a known calibration phantom, measuring a set of pixel values P through the phantom(s), identifying c values for those same pixels based on the phantom design, and fitting θ to make Q≈P. There are many types of $f$ functions available in the literature for this type of purpose, including polynomials, splines, B-splines, radial basis functions, neural networks, and support vector machines (all of which are known in the art). Note that each spectral channel can (and in general will) have its own θ.

Like the explicit model, with perfect measurements and with θ being accurately known, one can effect material discrimination by recovering c for an unknown material by solving for the values of c that make Q match the measured detector values. The empirical-fit model approach can also tolerate mistakes in the physics model (including disregarding effects that cannot currently be accurately characterized by analytical models) and still be successful.

Measurement noise typifies a practical application setting. Electronic noise is typically Gaussian, whereas photon noise is generally Poisson distributed. In low-noise X-ray detectors, for example, if Q is the true transmission through some object, then the measured signal is typically approximately Poisson distributed, with Poisson parameter (SNR$^2$×Q), where SNR is the signal-to-noise ratio through air. Therefore, the probability that one will measure some transmission P given that the underlying material is described by c can be written as:

$$Pr[P|Q] = \frac{(\alpha Q)^{\alpha P} e^{-\alpha Q}}{(\alpha P)!}$$

where $\alpha = SNR^2$, and note that Q is a function of c. One can then find the value of c that best explains P (i.e., find the value of c for which P is most likely) by searching for the value of c that makes Pr[P|Q] largest. In practice, however, the above equation may be difficult in some cases to maximize directly. Instead, one can equivalently find the value that minimizes log-likelihood (i.e. the negative log of probability), $$-\log Pr[P|Q] = \alpha(Q_n - P_n \log Q_n) + \text{(constant)}$$

where the constant term can be ignored. This equation is often much easier to minimize. With multiple spectral channels, one can combine the likelihood functions for the different spectral channels and estimate c by finding the value that minimizes $$D(c) = \sum_n w_n (Q_n - P_n \log Q_n)$$

where $P_n$ is the detector measurement under the n'th spectrum, $Q_n$ is the Q equation using the n'th spectrum $\varphi_n$ (for an explicit physics model) or spectral parameters $\theta_n$ (for an implicit physics model), and $w_n$ is a weight (usually equal to $\alpha_n$) reflecting the confidence or SNR of the n'th spectrum.

The D function is referred to herein as the fidelity criterion. Other fidelity criteria that are less theoretically motivated (but perhaps more convenient to work with) could also be used, including:

$$D(c) = \sum_n w_n (Q_n - P_n)^2$$

$$D(c) = \sum_n w_n (\log Q_n - \log P_n)^2$$

$$D(c) = \sum_n w_n |Q_n - P_n|$$

$$D(c) = \sum_n w_n |\log Q_n - \log P_n|$$

$$D(c) = \sum_n \frac{w_n}{P_n} (Q_n - P_n)^2$$

Those skilled in the art will appreciate that such a model readily supports dual-energy, more than two source energies (3, 4, 100, etc.), continuously-variable source energies, variable source filtration (such as a filter wheel), detectors with energy selectivity such as a stacked detector, or several or all of these at once. The models also apply to a variety of acquisition types. For example, the different modalities and spectral channels can image an object all at the same time, they can be interlaced within a single scan, or the object can be scanned multiple times with different modalities or spectral channels.

In a typical embodiment, such approaches can produce an output image for which each pixel contains a separate c value. The D functions for each pixel can be combined so that total fidelity cost is:

$$D = \sum_n w_n \sum_{i,j} (Q_n(i,j) - P_n(i,j) \log Q_n(i,j))$$

where $Q_n(i,j)$ is calculated from the c vector from pixel (i,j). By one approach all P images are the same size, are well-aligned, and c is the same size as each P. By another approach, c and P may have different resolutions, not all P images may be the same size, and the P images need not be well aligned. (i,j) denote the pixel indices for the P image, and the Q function pulls from the c image as necessary to get the portion of c that overlaps with the (i,j)'th pixel from P. This can be done by either taking the c pixel closest to the (i,j)'th pixel in P, or by averaging (or performing a weighted average) of the pixels in c that overlap with the area covered by the imaging system's (i,j)'th pixel for image P.

The Q function can also be used to generate a virtual image from the c data. For example, when c is higher resolution than P, the Q function can be used to synthesize a high-resolution version of P. To illustrate, a dual-energy X-ray system might acquire an interlaced image of size 1400×6000, where odd columns are high-energy and even columns are low-energy, so $P_1$ and $P_2$ are each 1400×3000. One can choose c to be 1400×6000, and one can similarly choose to evaluate $Q_1$ and $Q_2$ at every c pixel, so $Q_1$ and $Q_2$ are also 1400×6000. Then D is evaluated using $P_1$ versus the odd columns of $Q_1$, and $P_2$ versus the even columns of $Q_2$. Using this D, one then recovers a c image. Then one can evaluate $Q_1$ to get a 1400×6000 version of $P_1$, which is higher resolution than the original $P_1$. This process can also be performed using Q functions for spectra or modalities that were never acquired. For example, in the above example say that $P_1$ is a 6 MV X-ray spectrum, and $P_2$ is a 3 MV X-ray spectrum, then one can evaluate Q using an explicit physics model with a 450 kV spectrum to create a virtual 450 kV image, even though no such data was acquired. Such an approach permits one, for example, to form a virtual image at a same resolution as a corresponding material-identification image for a real or virtual spectral channel of a real or virtual modality by feeding the material-identification information through an imaging model for that modality and spectral channel.

In many application settings there will be non-idealities in the imaging chain, with scatter and sneak paths being two examples in these regards. If desired, these and other effects can be accommodated by further modifying the Q formula (before feeding it into D). For example, sneak paths or background scatter (such as, for example, object-independent scatter) can be included by adding a parameter b to Q, $$Q = b + \int \varphi(E) e^{-\sum_{k=1}^{K} A_k(E) c_k} dE$$

where this b parameter can be calibrated ahead of time. These teachings will further accommodate using different b values for different channels and/or scan positions, but the values can be independent of the scan object (and hence independent of c and P).

Object-dependent scatter can similarly be accommodated by adding some term S, $$Q = S + \int \varphi(E) e^{-\sum_{k=1}^{K} A_k(E) c_k} dE$$

or $$Q = b + S + \int \varphi(E) e^{-\sum_{k=1}^{K} A_k(E) c_k} dE$$

where S can now be object-dependent and hence calculated from the c and/or P values. This scatter calculation could use an explicit model, like the Klein-Nishina formula (for Compton scattering) or table-lookups (for pair-production or photo-electric effect). In the alternative, these teachings will also accommodate employing a more empirical model that may or may not be associated with any particular physics formulae. For example, this could comprise using scatter-kernel methods (used, for example, in flat panel scatter correction) (which might be considered somewhat akin to an empirical model). Other physics effects, such as X-ray crosstalk, optical crosstalk, detector lag, or electronic non-linearities can all be similarly modeled if desired.

Generally speaking, each physics effect modeled in Q can be explicit or empirical, and the two types can be mixed. That is, one can use explicit spectrum/transmission calculations with an empirical scatter model, or vice versa.

The Q model can also be modified to take in extra information. This can comprise using, for example, out-of-plane sneak/scatter detectors to estimate S explicitly. Or it can comprise the use of beam quality detectors (as described, for example, in U.S. Pat. No. 7,780,352 entitled Radiation System and Radiation Beam Quality Detector and Method, the contents of which are fully incorporated herein by this reference) that measure changes in spectrum on a view-by-view basis by, for the explicit model, modifying the $\varphi(E)$ spectrum on a view-by-view basis, or, for the empirical model, using a beam-quality index as input to the empirical model.

These teachings can also support very different imaging modalities by using different Q functions (and perhaps modifying D to better reflect the noise properties of the other modality as appropriate). That is, while the Q model described above is particularly useful for X-ray-based images, alternate Q models could be utilized for optical imaging, neutron activation, passive radiation detection, backscatter imaging, ultrasound, or mm-wave or THz imaging as desired. These Q models (even when from different modalities) could all be evaluated using the same set of c values, and combined into a single D term that is small when Q and P match (and hence c is consistent with the measurements) and large otherwise. So configured, the D term pertaining to fidelity is minimized only when the recovered image matches the measurements.

Note that the proper choice of basis materials may depend on spectral channel and even more so on modality. That is, the four basis materials that are appropriate for megavolt-range X-ray imaging may be different from the optimal material basis for kilovolt-range X-ray imaging, which might both be different from an appropriate basis for Terrahertz-range imaging. Furthermore, one might need more or fewer bases for some modalities than for others. When combining modalities, the number of bases in general should grow. For example, while four bases are sufficient for megavolt imaging, more than four might be needed if combining megavolt imaging with another modality.

In some application settings there may not be enough information to recover c from D alone. For example, dual-energy methodologies with four bases can lead to two equations and four unknowns. Furthermore, even if there are four or more effective spectra, the spectra may be somewhat redundant, and measurement noise is usually non-trivial. A feasibility model can serve to restrict the solution to c images that are physically plausible. Some examples of useful feasibility constraints include:

Non-Negativity: The estimates should not require negative amounts of any element;
Restricted Elements: Some elements cannot appear in the image.
Chemical Limits: Elements can only appear in amounts or ratios that are chemically sound;
Material-Type Smoothness: The material type will sometimes change abruptly (say, on boundaries between objects), but otherwise should be very smooth;
Mass or Density Smoothness: The amount of material should also be somewhat smooth.

The first three constraints presented above can be achieved by hyperplane bounding. The fourth and fifth constraints can be achieved by regularization (achieved, for example, via smoothing penalties).

One efficient way to restrict a search is by using a set of hyperplane boundaries by enforcing that $Bc \geq d$ where B is some matrix and d is some vector (often all zeros). This type of constraint can be handled very efficiently and is frequently addressed in prior art applied math literature.

The aforementioned non-negativity constraint physically specifies that the material can be explained without requiring negative amounts of any element. Anything that violates this constraint is not physically plausible. Mathematically, an equivalent statement is that there is some set of weights $\alpha_1$ to $\alpha_{95}$ such that $$\sum_k A_k(E)c_k = \sum_Z \alpha_Z \mu_{Z(E)}$$

and $\alpha_Z \geq 0$ for all Z. This can also be modified to also support the restricted elements constraint by, given some set of allowable materials, $Z_{allowed}$, requiring $$\sum_k A_k(E)c_k = \sum_{Z \in Z_{allowed}} \alpha_Z \mu_{Z(E)}$$

where $\alpha_Z = 0$ for all Z in $Z_{allowed}$. This approach produces $\mu(E)$ curves that can be represented as a non-negative sum of allowable elements. In matrix form, one limits the c's to those where there is some vector $\alpha \geq 0$ for which $Ac = \mu\alpha$, where $\mu$ is the matrix of $\mu_Z(E)$ curves for all allowable pure elements. This does not naturally look like a hyperplane constraint (i.e. a constraint of the form $Bc \geq d$), but it may nevertheless be turned into one.

Without intending any particular limitations in these regards, these teachings will support designing a set of hyperplane constraints B,d to enforce/enable such a non-negativity constraint as follows:

Choose an operator g. $g(i) \geq 0$ for all i. example: $g^t\mu = \mu(E_j)$;
Choose an operator h. Example: $h^t\mu$ is the derivative of $\mu$ at bin $E_j$;
Then find:

$$\rho_{min} = \min_m \frac{h^t\mu_m}{g^t\mu_m} \text{ and } \rho_{max} = \max_m \frac{h^t\mu_m}{g^t\mu_m};$$

where $\mu_m$ is the discretized attenuation curve for the m'th material in $Z_{allowed}$.

Add two zeros to d and new row vectors to B:

$$B_1 = (h - \rho_{min}g)^t A \text{ and } B_2 = (\rho_{max}g - h)^t A$$

This process can be repeated as appropriate to accommodate many different operators, where for each pair of g,h operators, two additional hyperplanes are added to B.

The above-described procedure can easily produce thousands of hyperplanes, but many of those hyperplanes will likely be essentially meaningless in practice. That is, if one hyperplane is satisfied, several others may be guaranteed to be satisfied as well. By one approach these essentially redundant hyperplanes can be removed from consideration. Furthermore, in settings where satisfying one hyperplane almost implies that another hyperplane is satisfied, then one may again, if desired, disregard or delete that second hyperplane.

Accordingly, one can establish effective hyperplane bounding for feasibility constraints using only, for example, 10 to 15 hyperplanes. Again without intending any particular limitations in these regards, the following pruning procedure can effect such an approach:

For j=1 to (number of constraints in B):
Find:

$$\delta = \min_{w:w\geq 0} \left\| B_j - \sum_{i\neq j} w_i B_i \right\|^2$$

using a convex-optimization solver such as Sedumi or SDPT3 (software programs for Matlab for solving semi-definite, quadratic, or linear problems);

When δ is zero (or very small), prune away $B_j$.

By one approach these teachings will accommodate building a chemical feasibility database for cargo scanning that holds for either all cargo, all cargo at a particular site, or that is dependent on the cargo's manifest. By another approach, these teachings will accommodate building a chemical feasibility database for medical scanning that holds for all images, for only specific body parts, for only specific patients, or for only specific body parts of specific patients (for example, some patients might have metal fillings whereas some other patients may be known to have no metal fillings). Each chemical element is designated as capable of existing in a pure form, as permissibly existing only in combination with some other material subject to some maximum ratio; or as not being permissible at all. By way of illustration, iron might be designated as capable of existing in a pure form while any sodium (or, say, any alkali metal) atom must have at least one associated halogen atom or hydroxide ion, while rare earth elements are not permissible in a cargo setting whatsoever. Similarly, for medical scanning, many elements and materials can likely be similarly eliminated if they are unlikely or unable to occur in the body. Furthermore, for industrial non-destructive testing, many elements can again likely be eliminated when it is highly unlikely (or impossible) for such elements to appear in the manufacturing process.

These rules are flexible in practice and there is considerable room to accommodate a wide range of application settings and needs. Elements or materials that are not permissible at all can be excluded by excluding them from $Z_{allowed}$ in the non-negativity constraint. Other constraints can be handled by enforcing ranges of ratios. Say, for example, that there are N limiting formulae for element Z, and let $w_{n,Z}$ describe the relative amount of each element for formula n. A corresponding useful search might then only consider c vectors for which there is some α for which Ac=μα and:

$$\alpha_z \leq \max_n w_{n,z} \min_{z'} \frac{a_{z'}}{w_{n,z'}}$$

In a given application setting this can likely be turned into a set of appropriate hyperplanes on c.

The applicant has determined that in many cases material type changes smoothly within the image. That is, an organic pixel is usually neighbors with other organic pixels, steel pixels are usually neighbors with other steel pixels, lead pixels will usually be neighbors with other lead pixels, and bone pixels will usually be neighbors with other bone pixels.

Similarly, material amount also usually changes slowly. The term "material amount" can mean different things, depending on the application setting. For three-dimensional imaging, material amount may mean the amount of mass in each voxel. Or similarly, as is typical in computed tomography, material amount may indicate the volume density of the material (such as in g/cm^3). For two-dimensional imaging, material amount could refer to path length, i.e. the total path length of material that is represented in a given pixel. Material amount could also refer to the product of path length and density. Material amount could also refer to the total mass per pixel (such as in grams), or similarly, it could refer to projected density (such as in g/cm^2). Projected density (which is particularly useful for X-ray radiography) can be obtained, for example, by integrating the volume density of an object over the integral of the region imaged by a pixel. Some of these are often equivalent; for example projected density can be seen as a generalization of path length×density; additionally "path length" can sometimes be used as a shorthand term that actually means projected density. Using any of these definitions, in typical objects, material amount is usually somewhat smooth. For example, pixels representing 12 inches of water are usually neighbors with other pixels that also contain near 12 inches of water while a pixel that contains 6 inches of steel will often be neighbors with other pixels containing near 6 inches of steel.

By one approach these teachings provide for treating each pixel as a vector (and, for megavolt X-ray imaging, more specifically as a 4-vector, i.e. a vector in four dimensions). Using this approach the direction of the vector can indicate the material type while the length indicates roughly the material density or amount. To encourage material-type smoothness this process can favor having neighboring vectors point in similar directions. Similarly, to encourage material-amount smoothness, this process can favor having neighboring vectors of similar lengths. These smoothness constraints (regarding vector direction and length) can be enforced separately or can be combined as desired.

Smoothness can be added as a constraint by, instead of just minimizing D, instead minimizing D+λR, where λ is a weighting factor and R is a penalty function that encourages smoothness.

To enforce neighboring vectors to have similar values (which is the product of direction and length), one can choose the $L_2^2$ gradient norm (i.e., Tikhonov regularization):

$$R = \sum_{x,y} (\|c_{x,y} - c_{x-1,y}\|^2 + \|c_{x,y} - c_{x,y-1}\|^2)$$

As another approach in these regards one can employ so-called Total-Variation (TV) regularization (this particular case is called Vector-TV regularization):

$$R = \sum_{x,y} \sqrt{\|c_{x,y} - c_{x-1,y}\|^2 + \|c_{x,y} - c_{x,y-1}\|^2}$$

To enforce neighboring vectors to have similar lengths, this process can be configured to calculate magnitudes prior to the above regularization formulae. So configured, for example, one can choose either the $L_2^2$ norm of the gradient of the magnitudes:

$$R = \sum_{x,y} ((\|c_{x,y}\| - \|c_{x-1,y}\|)^2 + (\|c_{x,y}\| - \|c_{x,y-1}\|)^2)$$

or Total-Variation of the magnitudes:

$$R = \sum_{x,y} \sqrt{(\|c_{x,y}\| - \|c_{x-1,y}\|)^2 + (\|c_{x,y}\| - \|c_{x,y-1}\|)^2}.$$

There are many other popular regularization functions, including $L_1$ regularization (i.e., anisotropic TV), Huber functions, hyperbolic $L_1$ or TV approximations, and so forth that could all be used in place of $L_2^2$ or TV as desired.

To enforce having neighboring vectors point in similar directions, these teachings will accommodate any approach that penalizes (at least in part) an angle differential (or a term that includes, at least implicitly, the angle differential) between neighboring vectors such as the $CF_1^1$ penalty:

$$R = \sum_{x,y} (\|c_{x,y}\|\|c_{x-1,y}\| + \|c_{x,y}\|\|c_{x,y-1}\| - (c_{x,y} \cdot c_{x-1,y}) - (c_{x,y} \cdot c_{x,y-1}))$$

or the $CF_1^{1/2}$ penalty:

$$R = \sum_{x,y} \left( \sqrt{\|c_{x,y}\|\|c_{x-1,y}\| - (c_{x,y} \cdot c_{x-1,y})} + \sqrt{\|c_{x,y}\|\|c_{x,y-1}\| - (c_{x,y} \cdot c_{x,y-1})} \right)$$

or vector-cosine-similarity:

$$R = \sum_{x,y} \left( 2 - \frac{c_{x,y} \cdot c_{x-1,y}}{\|c_{x,y}\|\|c_{x-1,y}\|} - \frac{c_{x,y} \cdot c_{x,y-1}}{\|c_{x,y}\|\|c_{x,y-1}\|} \right).$$

Multiple regularizers can be combined by minimizing $$D + \lambda_1 R_1 + \lambda_2 R_2 + \ldots$$

By way of illustration, these processes will accommodate using either a single R term that enforces similar neighboring values, magnitudes, or directions. They will also accommodate two R terms with one term enforcing similar neighboring magnitudes and the other term for similar directions. These teachings will also accommodate combining all three types and/or more than one of each type simultaneously as desired. These R terms can also be derived as statistical priors. That is, the basic goal can be to find the c that is most likely given the measured P data. Equivalently, one may wish to find c to maximize $Pr[c|P]$. Note that, using Bayes' theorem, this can be rewritten as $$Pr[c|P] = \frac{Pr[P|c]Pr[c]}{Pr[P]}.$$

Furthermore, maximizing $Pr[c|P]$ is equivalent to minimizing $-\log Pr[c|P]$, which is $$-\log Pr[c|P] = D(c) - \log Pr[c] + (\text{constant})$$

where the constant term can be ignored, and D is the Fidelity term described earlier. Accordingly, one can equate $Pr[c]$ with $e^{-\log R}$, or equivalently, R can be thought of as $-\log Pr[c]$. That is, one can choose R functions simply because they seem to give better images, or one can choose R terms more rigorously by establishing statistical priors on the distribution of c values and then take the log of those priors. All feasibility constraints can be thought of with either of these philosophies.

A corresponding search problem is to find c to minimize $D+\lambda R$ subject to $Bc \geq d$. There are at least two main approaches to handling the hyperplane constraint in these regards. B and c together define a set of hyperplanes that constitute a barrier (i.e. a boundary-surface in c-space), where solutions on one side of the barrier (or directly on the barrier) are preferred, and solutions on the other side of the barrier are to be avoided if possible. Per a hard-barrier approach, one constrains the search algorithm to never look outside the hyperplane barrier (i.e., only search over the range of c values for which $Bc \geq d$). Equivalently, this comprises minimizing $D+\lambda R+C$, where $C=0$ when $Bc \geq d$, and $C=\infty$ otherwise. This is equivalent to using a statistical prior where $Pr[c]=0$ when $Bc<d$.

Per a soft-barrier approach, one minimizes $D+\lambda R+C$ where C becomes larger in the direction of violating the hyperplane constraint and smaller in the direction of satisfying the hyperplane constraint. This can be done in such a way that C is differentiable, and thus can be easier to minimize than the hard-barrier approach (for example, any optimization algorithm based on derivatives can have a hard time taking the derivative of a function whose value is $\infty$, and an especially hard time coping with the barrier itself, where the derivative is infinite for the hard barrier approach). Two common approaches for soft barriers are the quadratic barrier (where C is quadratic) and the log-barrier (where C is based on a logarithm). For the quadratic barrier approach, the barrier is initially enforced only loosely, so the solution may make an excursion beyond the barrier. For the logarithmic approach, the barrier is initially enforced very strongly, so the solution must stay far inside the barrier. As the process progresses, the weights can be adjusted (for example, strengthened for the quadratic barrier approach and relaxed for the log barrier approach) so that the barrier eventually becomes nearly identical to the C shown for the hard barrier, above.

That said, there are many search algorithms known in the art for minimizing cost functions that can be readily employed for the present purposes. A few of these known approaches are as follows.

Gradient-based methods are appropriate when all terms are differentiable. Accordingly, these methods are suitable for use with a soft-barrier and a differentiable penalty (including, for example, Tikhonov regularization or hyperbolic TV approximation, while excluding, for example, TV). These can include first-order gradient-based methods, including conjugate gradient or steepest descent as well as quasi-Newton methods, including L-BFGS. In some cases these methods can also be modified to cope with hard barriers. These methods can also be modified to cope with non-differentiable or non-convex functions, for example by using surrogates (usually parabolic surrogates) or optimization-transfer methods, or by modifying the cost function such as by using hyperbolic approximations.

Other methods also include proximal splitting methods that are particularly appropriate for non-differentiable functions. Such an approach can facilitate, for example, searching for one set of c values that minimize D (plus some extra penalty) and another set of c values that minimize λR (plus some other extra penalty) where those extra penalties are chosen in a way that these two c's will eventually (after enough iterations) become equivalent (and both will minimize D+λR).

In the case where one is actually minimizing $D+C+\lambda_1 R_1 + \lambda_2 R_2 + \lambda_3 R_3 \ldots$, this process can be configured to have a separate c guess for each term. Or, as another approach, one can collect some suitable terms (for example, find one c estimate for all differentiable terms together, and separate c terms for each non-differentiable term). The Alternating-Direction Method of Multipliers (ADMM) method is a well-known method for solving such a problem when there are only two simultaneous guesses. This method has many variations, including for inexact solution of sub-problems (using cutting planes, gradient descent, proximal penalties, or predictor/corrector modification) or acceleration factors, and has also been extended to handle more than 2 costs (including Figueredo's M-ADMM, Boyd et al's consensus-ADMM, and Combette and Pesquet's Parallel-Proximal-Algorithm), though some variations have features that are not necessarily compatible with other variations.

At least one advantage of these methods is that by splitting the problem into several sub-problems, the sub-problems can be much easier or efficient to solve, and can often be solved exactly, even for non-differentiable functions. For example, TV regularization and the C function for hard-barrier are both difficult to solve with gradient-based methods, but with proper splitting methods, their sub-problems can be solved exactly and efficiently by proximal methods.

Some terms, such as the aforementioned fidelity term, or some direction-based material-smoothness regularizers, on the other hand, might have no known exact proximal solution. That said, however, their sub-problems may often be solved, at least approximately, by methods such as gradient-based methods, trust-region-based methods, or proximal-point-based methods.

Numerous methods can also be used to speed up the optimization. For example, one can perform a multi-resolution approach that first estimates a low-resolution image, then uses that as an initialization to estimate a higher resolution image, then an even higher resolution image, and so forth until the full image is estimated.

These teachings will also accommodate displaying the image as the search progresses. This might comprise, for example, showing a low-resolution result first, then updating the display as higher resolution results become available. As another example, this might comprise showing a noisy/unrealistic image at first, and continually updating the display as the c values are updated in background processing. This could also allow the user to adjust regularization parameters (like the λ values) and have the display gradually catch up as the processing progresses.

For many application settings it will be useful to present the recovered material descriptors in some fashion to the user. However, these values are usually not particularly meaningful to display directly to a user. For example, a user is usually not directly interested in a list of material-bases coefficients (such as a list of 4 coefficients), especially since the bases may include imaginary materials, but rather they are likely interested in understanding what materials or range of materials correspond to these coefficients. Therefore these material descriptors may be converted into something more suitable to displaying to an end user. By one approach this might comprise coloring the pixels according to a corresponding material number. By another approach this might comprise displaying a numeric effective atomic number ($Z_{eff}$) value. This could be done in a variety of ways. For example, the appropriate number (such as, say, "13" for aluminum) could appear when hovering a cursor over the pixel. By another approach, this might comprise displaying a numeric (and even arbitrary) class number (such as, say, "2" for aluminum) (where the class numbering could employ a continuous numbering paradigm (that would accommodate, for example, a number such as "2.7") or a more discrete paradigm (that limits, for example, the numbers to integer values)). By yet another approach one could provide a text-based list regarding what materials this might be.

These teachings are also well suited to support automatic analysis (for example, to automatically analyze resultant material numbers for suspicious values or patterns). Some automatic analysis could be performed directly on the aforementioned c values. Other automatic analysis could be performed on the $Z_{eff}$ value or class number derived from c.

By another approach, all of these could be aided by matching the estimated c to a list of candidate c values that serve as material templates. So configured, one can identify which template of a plurality of such templates is closest to a recovered c value for a given pixel by looking at some distance (or the like) between the template vector and the c vector. There are several types of material distance that will serve well in these regards, including the angle differential between two vectors:

$$\theta = \cos^{-1} \frac{(c \cdot t)}{\|c\| \|t\|}$$

Another type of material distance relies upon a cost-based approach. For example, one can model Pr[Q|c] with a second-order Taylor series and then try replacing c with each template vector. Using this approach, the "material distance" relates to an amount by which cost changes with each template.

By another approach, one can identify mixtures by looking for pairs (or higher order combinations) of template materials for which the material distance between c and the mixture of templates is small.

Generally speaking, these teachings provide for finding a $Z_{eff}$ value for each pixel by finding which template material(s) have a smallest distance from the corresponding estimated c. When there is one clear winner, that winning template essentially identifies the $Z_{eff}$ value (since each template can be assigned a $Z_{eff}$ number). When there is more than one clear winner, but the competing candidates all have similar $Z_{eff}$'s, then the $Z_{eff}$ value can be the average of those $Z_{eff}$'s (possibly inversely weighed by the material distance). When mixtures are identified, $Z_{eff}$ can be a weighted average of the $Z_{eff}$'s of the mixture components. These techniques can similarly be used to find a class value for each pixel by assigning each template a class value instead of or in addition to a $Z_{eff}$ value.

In any of these cases, these teachings will accommodate using an existing coloring method that uses, for example, only $Z_{eff}$ or a class value rather than the 4-dimensional c vector. Similarly, one can display that $Z_{eff}$ or class value to the user numerically via an appropriate inspection tool of choice and automated analysis can also process that $Z_{eff}$ or class value.

In cases where a material distance is made small by at least two materials that are very different from each other, there are a variety of ways by which one can respond. For example, one can take whichever of the materials appears best. Or, one can treat the pixel as ambiguous. To treat the pixel as ambiguous, for example, one can color that pixel a color that corresponds to this state (such as the color gray) as well as display some indicator such as "unknown" in place of a numerical $Z_{eff}$ value. (See generally U.S. patent application Ser. No. 12/779,538 entitled Method and Apparatus Pertaining to Rendering an Image to Convey Levels of Confidence With Respect to Materials Identification, the contents of which are fully incorporated herein by this reference.) As yet another example, one can employ multiple values for the pixel in question. For example, one can dither or stripe the colors associated with the different $Z_{eff}$ or class values for the two or more template materials that minimize material distance from c. This can also include displaying the multiple values to the user, numerically, and/or passing the set of multiple possible values to the analysis tool when applied.

These ditherings or stripings can also be influenced by the material distances. For example, when two very different template materials are the same material distance from the estimated material, one can use equal amounts of the colors for those two template materials. When the material distance is smaller for one template than the other, then in the dithering or striping one can use more of the color associated with the template with the smaller material distance and less of the color associated with the template with the larger material distance. This approach can naturally be extended beyond two materials, to similarly dither or stripe three or more materials.

By one approach, to show a list of possible materials in these regards, one can associate each template with a list of similar materials. The list of possible materials is then the union of the lists of similar materials taken from all reasonably-well-matching templates. The probabilities for each material could then be optionally weighted inversely based on the material distance. These teachings are highly flexible in practice. For example, as noted earlier, one material comprised of one element can be located behind another material comprised of another, different element. Pursuant to the present teachings, the c-vector for the combination of one material behind another material is simply the sum of the c-vectors of the two materials. Therefore, if one can identify, for example, a shielding material, one can simply subtract it from the sum in order to identify the second material positioned behind that shielding material. As an illustrative example in these regards, one can effect virtual-layer removal by subtracting a first material descriptor from a second material descriptor to recover a material descriptor for an object that is hidden behind an object comprised of the first material.

Figure 5:
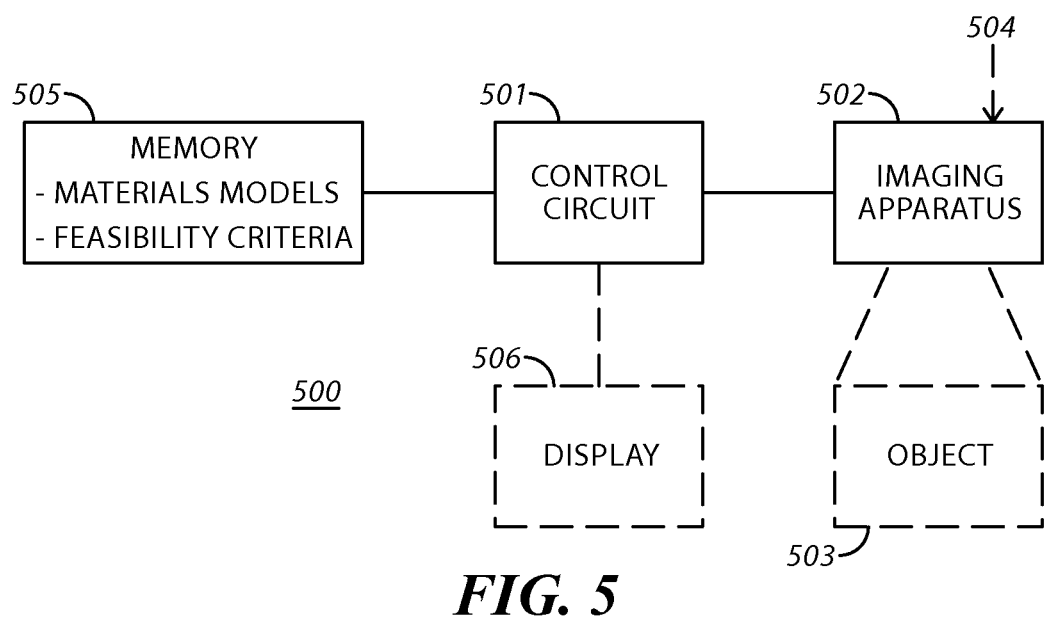
FIG. 5 comprises a block diagram as configured in accordance with various embodiments of the invention.

FIG. 5 presents an illustrative example of an apparatus 500 that accords with the present teachings. In this example the enabling apparatus 500 includes a control circuit 501 that operably couples to an imaging apparatus 502. This imaging apparatus 502 serves to capture imaging information for an object 503 such as, for example, a cargo container. This imaging apparatus 502 can comprise, for example, a non-invasive imaging apparatus having at least one modality with at least one spectral channel.

By one approach this imaging apparatus 502 comprises a multi-modality apparatus that produces multiple images of overlapping portions of the object 503 using different imaging modalities (such as X-rays (keeping in mind that the use of multi-energy X-rays alone may nevertheless be considered an example of a single-modality apparatus), magnetic-resonance imaging, ultrasound, neutron imaging, passive radiation monitoring, THz imaging, and so forth). By one approach, this can comprise producing these multiple images using differing spectral channels for a same modality of image capture (such as, for example, 6 MV X-rays and 3 MV X-rays).

These multiple spectral channels can be made available, for example, at least in part by varying an energy-source setting 504 for the imaging apparatus 502. By another approach, in lieu of the foregoing or in combination therewith, this can be facilitated by using one or more detectors that offer multiple spectral responses. These and other approaches for achieving multiple spectral channels can be achieved, for example, as described, in U.S. patent application Ser. No. 12/479,376, entitled Method and Apparatus to Facilitate Using Multiple Radiation-Detection Views to Differentiate One Material From the Other and fully incorporated herein by this reference.

The control circuit 501 also operably couples to a memory 505 (and, if desired, to an optional display 506). Such a control circuit 501 can comprise a fixed-purpose hard-wired platform or can comprise a partially or wholly programmable platform. These architectural options are well known and understood in the art and require no further description here. This control circuit 501 is configured (for example, by using corresponding programming as will be well understood by those skilled in the art) to carry out one or more of the steps, actions, and/or functions described herein.

The memory 505 may be integral to the control circuit 501 or can be physically discrete (in whole or in part) from the control circuit 501 as desired. This memory 505 can also be local with respect to the control circuit 501 (where, for example, both share a common circuit board, chassis, power supply, and/or housing) or can be partially or wholly remote with respect to the control circuit 501 (where, for example, the memory 505 is physically located in another facility, metropolitan area, or even country as compared to the control circuit 501).

This memory 505 can serve, for example, to non-transitorily store the computer instructions that, when executed by the control circuit 501, cause the control circuit 501 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM) or random access memory (RAM).)

This memory 505 may also serve to store all or part of the aforementioned plurality of models for different materials (that each provide a predicted result that the imaging information should present for a plurality of differing materials for a particular imaging modality and a particular spectral channel) and the feasibility criteria. By one approach, one or more of these models can provide information regarding how one or more different materials interacts with energy in a particular imaging modality (and hence may be dependent on modality but independent of imaging energy).

These teachings are highly flexible in these particular regards. For example, these detailed physics models may include a plurality of spectral models (that are, for example, independent of material) that each provide information on a particular spectral channel in a particular modality. Such spectral models may rely, for example, on use of a beam-quality detector.

As another example in these regards, these models may include one or more scanner models that describe the layout of the imaging apparatus 502. By one approach, such scanner models could be geometry based.

As yet another example in these regards, these models may include one or more imaging models that describe how multiple models (such as a spectral model and a material model) are combined to form a material-imaging model. These imaging models, when utilized, may be provided on a modality-by-modality basis.

And as yet one more example in these regards, these models may each be deterministic or they may be Bayesian or statistical. For example, a deterministic model might predict only the value that the imaging apparatus 502 is expected to produce. A statistical model might predict not only the expected value, but also the noise type (Poisson, Gaussian, etc) and the noise properties, such as the noise standard deviation.

In any event, such a control circuit 501 can be configured to process imaging information for the object 503 as provided by the imaging apparatus 502 to facilitate identifying materials. As described herein this can comprise using the plurality of models to identify candidate materials for portions of the imaging information and then using the feasibility criteria to reduce the number of candidate materials by avoiding at least one unlikely material or combination of materials.

As described herein, these materials can be described by a plurality of values that each corresponds to a different basis function (such as, for example, four basis functions. By one approach, at least one of these basis functions can correspond to an imaginary material ("imaginary" in the sense that the basis function mathematically describes something that does not and perhaps cannot exist in the physical world). For example, such a basis function can include negative amounts of a physical phenomena that is non-negative in nature. This can be accomplished, for example, by permitting the basis function to accommodate both positive and negative coefficients.

The aforementioned feasibility criteria can comprise, if desired, constraints regarding materials that are unlikely to be present in an absence of at least one other particular material and/or constraints regarding materials that are not physically possible as discussed above.

By one approach, at least one such feasibility criteria can serve to constrain multiple portions of the material-identification information to be similar to each other. This might comprise effectively smoothing the information by either smoothing a noisy answer or finding an answer that is most likely (and hence tends to exhibit a reasonable amount of smoothness).

Constraining adjacent portions of material-identification information to be similar to one another can comprise, for example, penalizing a measure of how large the gradient is of the material-identification pixels (or some corresponding function of those pixels such as the magnitude of the above-mentioned vectors). By another approach this can comprise penalizing a measure of the dissimilarity between the material types in each such portion. By yet another approach this can comprise penalizing a measure of the difference between the directions of the vectors of the material-descriptor values.

These teachings accommodate closed-loop processing that offers significantly greater accuracy than typical open-loop practices. The described detailed physics model makes highly-leveraged use of all available information. These teachings support the use of two or more imaging energies and/or layered detectors and are readily extendable to neutron-based imaging or even passive radiation techniques. By one approach one can employ detailed calibration methods to calibrate the physics model to a specific imaging apparatus. For example, one can employ a spectral calibration method to calibrate one or more spectral models. As another example, one can employ a scatter calibration method to calibrate one or more scatter models. As yet another example, one can employ a geometric calibration method to calibrate one or more scanner models. And as another example, one can employ a non-linear gain calibration method to calibrate one or more detector models.

The feasibility criterion or criteria, in turn, essentially leverages any of a variety of statistical priors for the objects being studied. In effect, these criteria facilitate determining which output images are inherently believable, which are unlikely but possible, and which are completely unbelievable.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept. For example, these teachings can readily enable new features such as mixture-discrimination and virtual shielding removal, the exploitation of multi-spectra and path-diversities for better accuracy and reduced false alarms, and will readily accommodate use in conjunction with leveraged information from manifests, current threat risks, or expected nuisance alarms.

As another example in these regards, one can effect these teachings by providing a cost function in combination with a corresponding optimization method. Such a cost function can include a fidelity term that is small when the imaging models are well satisfied and large when the opposite holds true. The cost functions can include a regularization term that is small when the feasibility criteria are well satisfied and large when this is not so. The optimization method itself may optionally limit its search to completely avoid considering some solutions that do not satisfy some feasibility constraints, or alternately include an extra term to enforce or encourage its constraints to be satisfied, either exactly or approximately.

And as yet another example in these regards, these teachings can be employed to identify material information for a first object and for the combination of the first object with a second object. One can then calculate a difference between these two material information results to calculate material-identification information for the second object alone.

I claim:
1. An apparatus comprising:
    a non-invasive imaging apparatus that directs at least one X-ray beam at an object to be imaged to thereby employ active X-ray imaging, and collects transmission measurements with at least one modality with at least one spectral channel;

a memory having stored therein:
  a plurality of models for different materials comprising a plurality of material-imaging models that each provide a predicted result that the transmission measurements should present for a plurality of differing materials for a particular modality and a particular spectral channel wherein the materials are described by a plurality of values that each corresponds to a different basis function;
  feasibility criteria, wherein the feasibility criteria comprises, at least in part, constraints that describe at least one material that does not exist in the physical world;
a control circuit operably coupled to the non-invasive imaging apparatus and the memory and being configured to process the transmission measurements for an object as provided by the non-invasive imaging apparatus to facilitate identifying materials as comprise the object by:
  using the plurality of models to identify candidate materials for portions of the transmission measurements;
  using the feasibility criteria to reduce the candidate materials by avoiding at least one of unlikely materials or combinations of materials to yield material-identification information.

2. The apparatus of claim 1 wherein the non-invasive imaging apparatus comprises a multi-spectral apparatus that produces multiple images of overlapping portions of the object using differing spectral channels.

3. The apparatus of claim 1 wherein the plurality of values comprises four values, one for each one of four different basis functions.

4. The apparatus of claim 1 wherein at least one of the different basis functions corresponds to an imaginary material.

5. The apparatus of claim 1 wherein at least one of the different basis functions will accommodate both positive and negative coefficients.

6. The apparatus of claim 1 wherein the feasibility criteria further comprises, at least in part, constraints regarding materials that are unlikely to be present in an absence of at least one other particular material.

7. The apparatus of claim 1 wherein the portions of the material-identification information comprise pixels of the material-identification information.

8. The apparatus of claim 1 wherein the feasibility criteria further comprises, at least in part, constraining multiple portions of the material-identification information to be similar to each other.

9. The apparatus of claim 8 wherein the other portions of the transmission measurements at least include portions of the material-identification information that are adjacent to each other.

10. The apparatus of claim 8, wherein constraining multiple portions of the material-identification information to be similar to each other comprises using similarity constraints regarding at least one of vector values, vector magnitudes, and vector directions.

11. The apparatus of claim 1 wherein the control circuit is further configured to:
  form a virtual image for a real or virtual band of a real or virtual modality by feeding the material-identification information through an imaging model for that modality and band.

12. An apparatus comprising:
a non-invasive imaging apparatus that at least employs active X-ray imaging, with at least one modality with at least one spectral channel;
a memory having stored therein:
  a plurality of models for different materials;
  feasibility criteria;
a control circuit operably coupled to the non-invasive imaging apparatus and the memory and being configured to process imaging information for an object as provided by the non-invasive imaging apparatus to facilitate identifying materials as comprise the object by:
  using the plurality of models to identify candidate materials for portions of the imaging information;
  using the feasibility criteria to reduce the candidate materials by avoiding at least one of unlikely materials or combinations of materials to yield material-identification information;
  effecting virtual-layer removal by subtracting a first material descriptor from a second material descriptor to recover a material descriptor for an object that is hidden behind an object comprised of the first material.

* * * * *